(12) United States Patent
Hladio

(10) Patent No.: US 10,512,430 B1
(45) Date of Patent: Dec. 24, 2019

(54) ANIMAL HEALTH TRACKING ASSEMBLY

(71) Applicant: Andrew Hladio, Ambridge, PA (US)

(72) Inventor: Andrew Hladio, Ambridge, PA (US)

( * ) Notice: Subject to any disclaimer, the term of this patent is extended or adjusted under 35 U.S.C. 154(b) by 0 days.

(21) Appl. No.: 16/175,903

(22) Filed: Oct. 31, 2018

(51) Int. Cl.
| | |
|---|---|
| *A61B 5/00* | (2006.01) |
| *A01K 27/00* | (2006.01) |
| *A01K 29/00* | (2006.01) |
| *A61B 5/0205* | (2006.01) |
| *A61D 99/00* | (2006.01) |
| *A61B 5/024* | (2006.01) |
| *A61B 5/11* | (2006.01) |

(52) U.S. Cl.
CPC .......... *A61B 5/6822* (2013.01); *A01K 27/001* (2013.01); *A01K 27/009* (2013.01); *A01K 29/00* (2013.01); *A61B 5/0205* (2013.01); *A61B 5/742* (2013.01); *A61D 99/00* (2013.01); *A61B 5/02438* (2013.01); *A61B 5/1112* (2013.01); *A61B 5/411* (2013.01); *A61B 5/4875* (2013.01); *A61B 2503/40* (2013.01); *A61B 2560/0214* (2013.01)

(58) Field of Classification Search
CPC ... A61B 5/6822; A61B 5/02438; A61B 5/411; A61B 2503/40; A01K 27/001
USPC ...................................................... 340/573.3
See application file for complete search history.

(56) References Cited

U.S. PATENT DOCUMENTS

| | | | | |
|---|---|---|---|---|
| 4,940,020 A | * | 7/1990 | Gordon ................ | A01K 27/001 119/802 |
| 5,001,463 A | * | 3/1991 | Hamburger .......... | G01N 1/2205 340/627 |
| 5,373,815 A | * | 12/1994 | Sagebiel ............. | A01K 27/005 119/654 |
| 5,923,254 A | * | 7/1999 | Brune ................. | A01K 15/021 340/573.1 |
| 6,019,066 A | * | 2/2000 | Taylor ................. | G11B 31/003 119/719 |
| 9,675,051 B2 | | 6/2017 | Bonge, Jr. | |
| 10,082,504 B2 | * | 9/2018 | Nelson ................ | G01N 33/68 |
| 2013/0014706 A1 | | 1/2013 | Menkes | |
| 2015/0181840 A1 | | 7/2015 | Tupin | |
| 2016/0120154 A1 | | 5/2016 | Hill | |
| 2016/0135431 A1 | | 5/2016 | Sheldon | |

* cited by examiner

*Primary Examiner* — John A Tweel, Jr.

(57) ABSTRACT

An animal health tracking assembly for tracking the physiological condition of an animal includes a collar that is wearable around a neck of an animal thereby placing the collar in physical contact with the animal. A control circuit is coupled to the collar and an electronic memory is coupled to the collar for storing a database. An allergen detector is coupled to the collar for detecting airborne allergens thereby tracking the animal's exposure to the airborne allergens. The allergen detector is electrically coupled to the control circuit and the control circuit communicates an identity of the airborne allergens to the electronic memory for storage in the database. In this way the electronic memory can track all of the airborne allergens to which the animal was exposed.

9 Claims, 4 Drawing Sheets

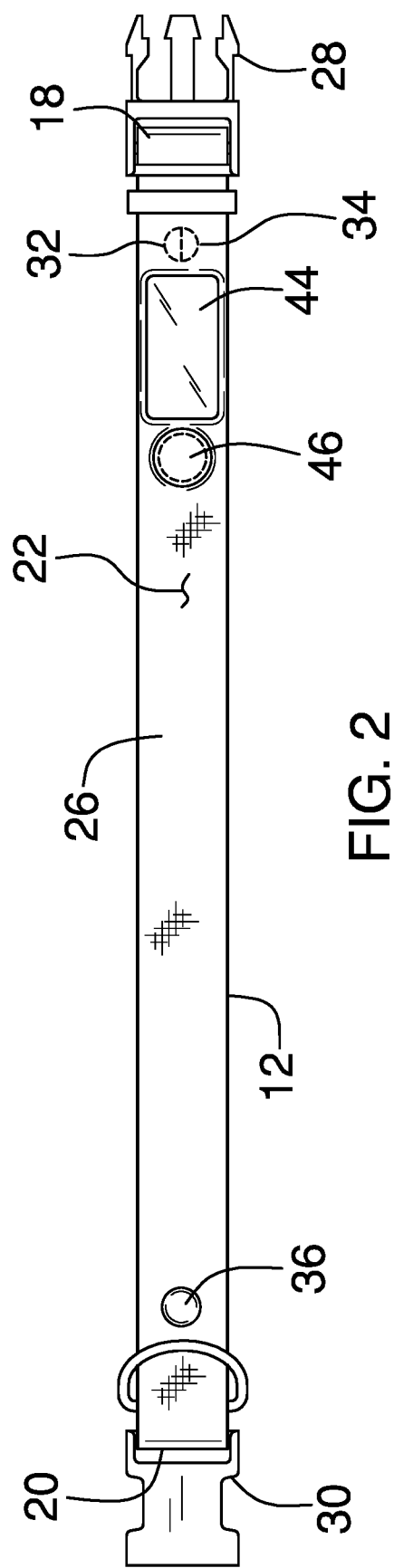
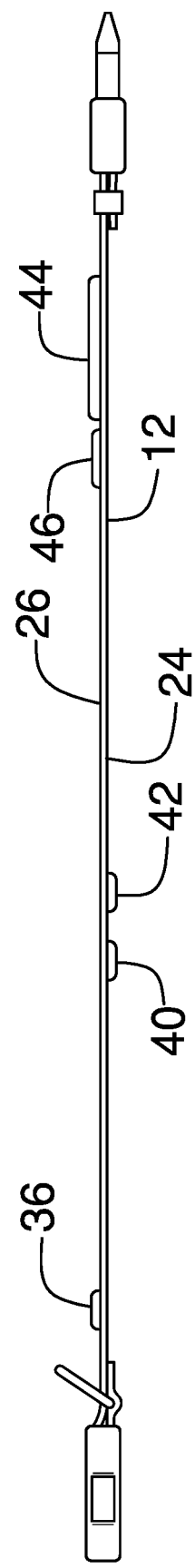
FIG. 2
FIG. 3

ANIMAL HEALTH TRACKING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to health tracking devices and more particularly pertains to a new health tracking device for detecting the physiological condition of an animal.

BRIEF SUMMARY OF THE INVENTION

An embodiment of the disclosure meets the needs presented above by generally comprising a collar that is wearable around a neck of an animal thereby placing the collar in physical contact with the animal. A control circuit is coupled to the collar and an electronic memory is coupled to the collar for storing a database. An allergen detector is coupled to the collar for detecting airborne allergens thereby tracking the animal's exposure to the airborne allergens. The allergen detector is electrically coupled to the control circuit and the control circuit communicates an identity of the airborne allergens to the electronic memory for storage in the database. In this way the electronic memory can track all of the airborne allergens to which the animal was exposed.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 2 is a front view of an embodiment of the disclosure.

FIG. 3 is a top view of an embodiment of the disclosure.

DETAILED DESCRIPTION OF THE INVENTION

Figure 1:
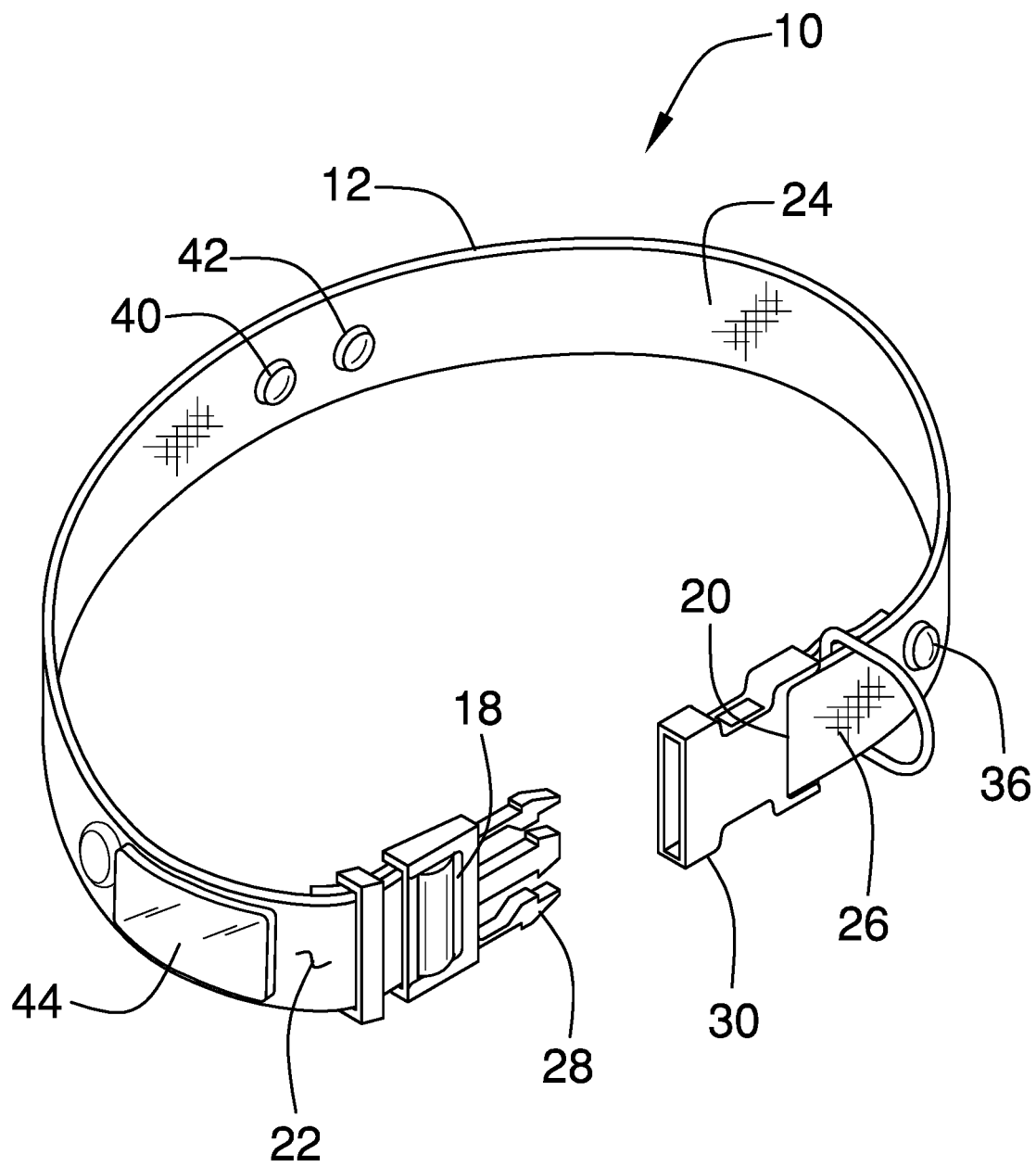
FIG. 1 is a perspective view of an animal health tracking assembly according to an embodiment of the disclosure.
Figure 4:
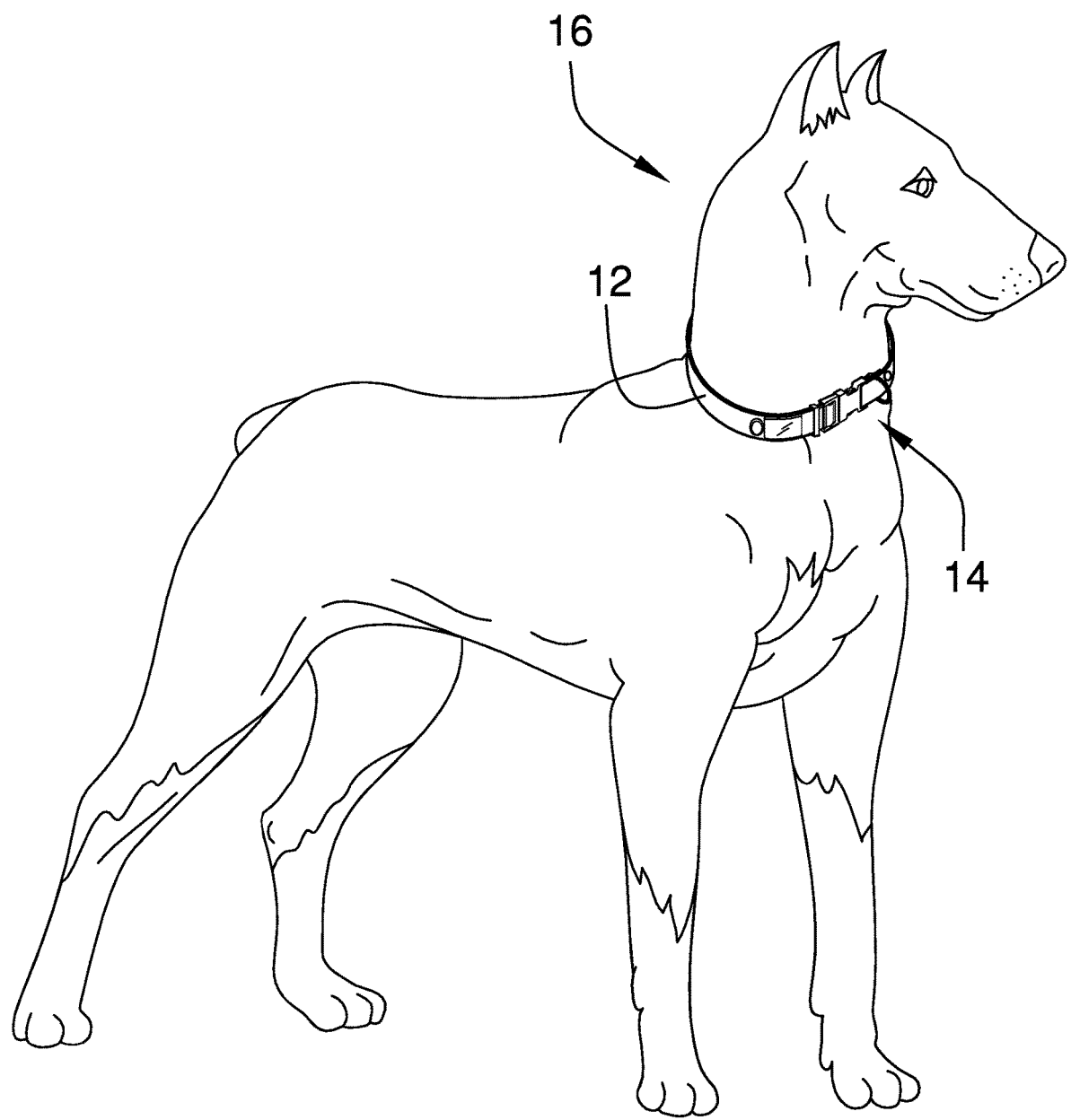
FIG. 4 is a perspective in-use view of an embodiment of the disclosure.
Figure 5:
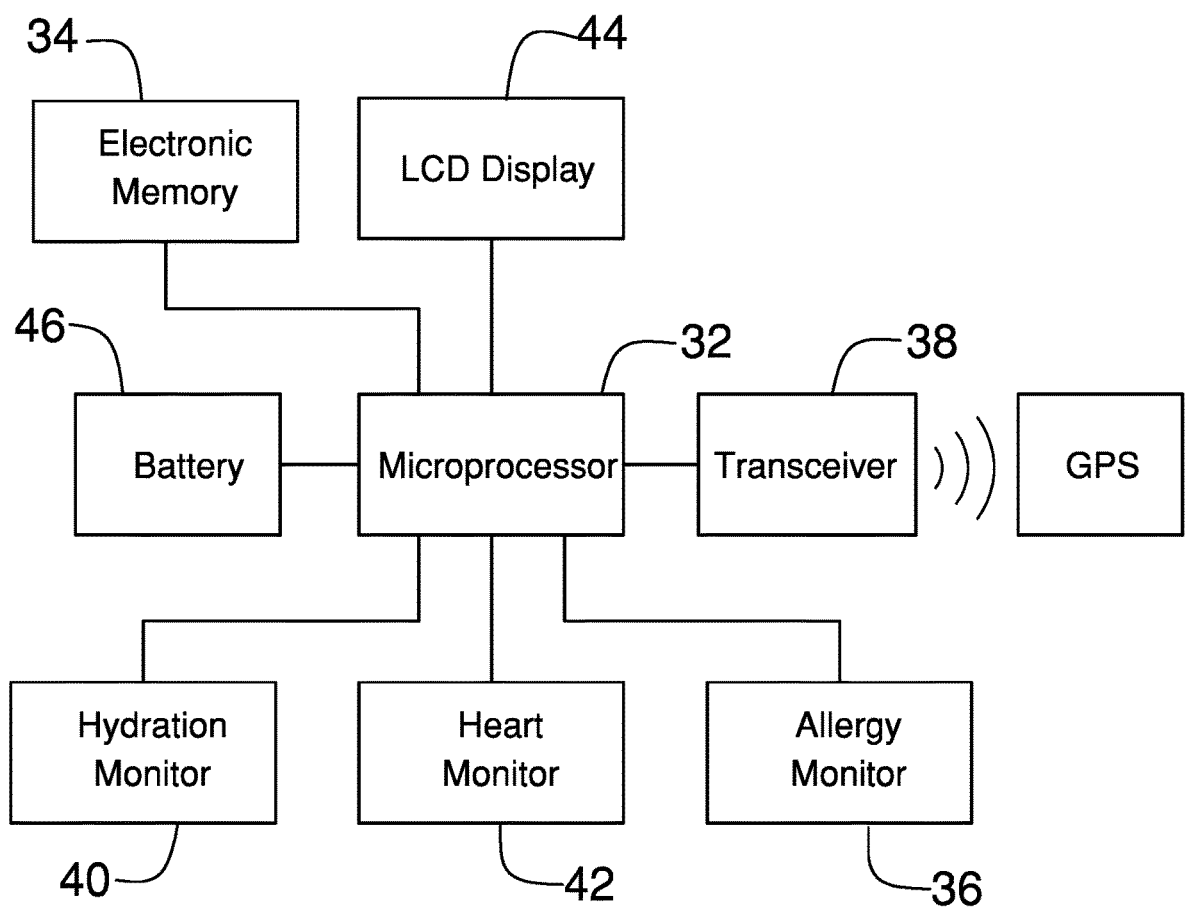
FIG. 5 is a schematic view of an embodiment of the disclosure.

With reference now to the drawings, and in particular to FIGS. 1 through 5 thereof, a new health tracking device embodying the principles and concepts of an embodiment of the disclosure and generally designated by the reference numeral 10 will be described.

As best illustrated in FIGS. 1 through 5, the animal health tracking assembly 10 generally comprises a collar 12 that is wearable around a neck 14 of an animal 16 such that the collar 12 is in physical contact with the animal 16. The animal 16 may be a domesticated animal, such as a dog, cat, livestock or any other animal commonly associated with human beings. The collar 12 has a first end 18, a second end 20 and an outer surface 22 extending therebetween. The outer surface 22 has a first side 24 and a second side 26, and the first side 24 abuts the animal's 16 neck 14 when the collar 12 is worn.

The first end 18 is matable to the second end 20 for retaining the collar 12 on the animal 16's neck 14. A first mating member 28 is coupled to the first end 18 of the collar 12 and a second mating member 30 is coupled to the second end 20 of the collar 12. The second mating member 30 releasably engages the first mating member 28 has the collar 12 forming a closed loop. Each of the first 28 and second 30 mating members may comprise complementary buckles or other type of releasable fasteners.

A control circuit 32 is coupled to the collar 12 and an electronic memory 34 is coupled to the collar 12. The electronic memory 34 is electrically coupled to the control circuit 32 and the electronic memory 34 stores a database. The electronic memory 34 may comprise digital data storage that is sufficiently small to be coupled to the collar 12, such as is employed in a mini SD card or the like.

An allergen detector 36 is coupled to the collar 12 for detecting airborne allergens thereby tracking the animal's 16 exposure to the airborne allergens. The allergen detector 36 is electrically coupled to the control circuit 32. Additionally, the control circuit 32 communicates an identity of the airborne allergens to the electronic memory 34 for storage in the database. In this way the electronic memory 34 can track all of the airborne allergens to which the animal 16 was exposed. Thus, any allergic reactions displayed in the animal 16 can be associated with one of the detected airborne allergens.

A transceiver 38 is coupled to the collar 12 and the transceiver 38 is in wireless electrical communication with a global positioning system (gps). In this way the transceiver 38 receives a physical location of the animal 16 from the gps. The transceiver 38 is electrically coupled to the control circuit 32 such that the physical location of the animal 16 is continuously updated in the database in the electronic memory 34. Moreover, the transceiver 38 may be a radio frequency transceiver or the like and the transceiver 38 may employ a WPAN signal and Bluetooth communication protocols. In this way the transceiver 38 can be synched with an electronic device, such as a Smartphone or the like, thereby facilitating the database in the electronic memory 34 to be downloaded for subsequent analysis.

A hydration monitor 40 is coupled to the collar 12 for sensing the hydration level of the animal 16. The hydration monitor 40 is positioned on the first side 24 of the outer surface 22 of the collar 12. In this way the hydration monitor 40 can be in physical contact with the animal 16. The hydration monitor 40 is electrically coupled to the control circuit 32 and the control circuit 32 communicates the hydration level of the animal 16 to the electronic memory 34.

A heart monitor 42 is coupled to the first collar 12 for sensing the animal 16's heartbeat. The heart monitor 42 is positioned on the first side 24 of the outer surface 22 of the collar 12. In this way the heart monitor 42 can be in physical contact with the animal 16. The heart monitor 42 is electrically coupled to the control circuit 32 and the control circuit 32 communicates the heartbeat to the electronic memory 34.

A display 44 is coupled to the collar 12 and the display 44 is electrically coupled to the control circuit 32. The display 44 displays indicia comprising operational parameters of each of the allergen detector 36, the hydration monitor 40 and the heart monitor 42. The display 44 is positioned on the second side 26 of the outer surface 22 of the collar 12 such that the display 44 is visible to an observer. Moreover, the display 44 may be an LCD or other type of electronic display 44. A power supply 46 is coupled to the collar 12 and the power supply 46 is electrically coupled to the control circuit 32. The power supply 46 is positioned on the second side 26 of the outer surface 22 of the collar 12 and the power supply 46 comprises at least one battery.

In use, the collar 12 is worn around the animal 16's neck 14 such that the heart monitor 42 and the hydration monitor 40 are in physical contact with the animal 16. Thus, the heart monitor 42 detects the animal 16's heartbeat and the hydration monitor 40 detects the animal 16's hydration level. Additionally, the allergen sensor senses the airborne allergens that the animal 16 to which the animal 16 is exposed. In this way the animal 16's physiological condition can be continuously monitored. Moreover, allergic reactions in the animal 16 can be correlated with the airborne allergens that were detected thereby facilitating the animal 16's health to be enhanced. The transceiver 38 facilitates the physical location of the animal 16 to be tracked via gps.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An animal health tracking assembly being configured to be worn on an animal for tracking both the animal's movement and the animal's physiological condition, said assembly comprising:
    a collar being wearable around a neck of an animal wherein said collar is configured to be in physical contact with the animal;
    a control circuit being coupled to said collar;
    an electronic memory being coupled to said collar, said electronic memory being electrically coupled to said control circuit, said electronic memory storing a database; and
    an allergen detector being coupled to said collar for detecting airborne allergens wherein said allergen detector is configured to track the animal's exposure to the airborne allergens, said allergen detector being electrically coupled to said control circuit, said control circuit communicating an identity of the airborne allergens to said electronic memory for storage in said database wherein said electronic memory is configured to track all of the airborne allergens to which the animal was exposed.

2. The assembly according to claim 1, wherein said collar has a first end, a second end and an outer surface extending therebetween, said outer surface having a first side and a second side, said first side abutting the animal's neck when said collar is worn, said first end being matable to said second end for retaining said collar on the animal's neck.

3. The assembly according to claim 2, further comprising:
    a first mating member being coupled to said first end of said collar; and
    a second mating member being coupled to said second end of said collar, said second mating member releasably engaging said first mating member having said collar forming a closed loop.

4. The assembly according to claim 1, further comprising a transceiver being coupled to said collar, said transceiver being in wireless electrical communication with a global positioning system (gps) wherein said transceiver is configured to receive a physical location of the animal, said transceiver being electrically coupled to said control circuit such that the physical location of the animal is continuously updated in said database in said electronic memory.

5. The assembly according to claim 2, further comprising a hydration monitor being coupled to said collar wherein said hydration monitor is configured to sense the hydration level of the animal, said hydration monitor being positioned on said first side of said outer surface of said collar wherein said hydration monitor is configured to be in physical contact with the animal, said hydration monitor being electrically coupled to said control circuit, said control circuit communicating the hydration level of the animal to said electronic memory.

6. The assembly according to claim 5, further comprising a heart monitor being coupled to said first collar wherein said heart monitor is configured to sense the animal's heartbeat, said heart monitor being positioned on said first side of said outer surface of said collar wherein said heart monitor is configured to be in physical contact with the animal, said heart monitor being electrically coupled to said control circuit, said control circuit communication the heartbeat to said electronic memory.

7. The assembly according to claim 6, further comprising a display being coupled to said collar, said display being electrically coupled to said control circuit, said display displaying indicia comprising operational parameters of each of said allergen detector, said hydration monitor and said heart monitor, said display being positioned on said second side of said outer surface of said collar wherein said display is configured to be visible to an observer.

8. The assembly according to claim 2, further comprising a power supply being coupled to said collar, said power supply being electrically coupled to said control circuit, said power supply being positioned on said second side of said outer surface of said collar, said power supply comprising at least one battery.

9. An animal health tracking assembly being configured to be worn on an animal for tracking both the animal's movement and the animal's physiological condition, said assembly comprising:
- a collar being wearable around a neck of an animal wherein said collar is configured to be in physical contact with the animal, said collar having a first end, a second end and an outer surface extending therebetween, said outer surface having a first side and a second side, said first side abutting the animal's neck when said collar is worn, said first end being matable to said second end for retaining said collar on the animal's neck;
- a first mating member being coupled to said first end of said collar;
- a second mating member being coupled to said second end of said collar, said second mating member releasably engaging said first mating member having said collar forming a closed loop;
- a control circuit being coupled to said collar;
- an electronic memory being coupled to said collar, said electronic memory being electrically coupled to said control circuit, said electronic memory storing a database;
- an allergen detector being coupled to said collar for detecting airborne allergens wherein said allergen detector is configured to track the animal's exposure to the airborne allergens, said allergen detector being electrically coupled to said control circuit, said control circuit communicating an identity of the airborne allergens to said electronic memory for storage in said database wherein said electronic memory is configured to track all of the airborne allergens to which the animal was exposed;
- a transceiver being coupled to said collar, said transceiver being in wireless electrical communication with a global positioning system (gps) wherein said transceiver is configured to receive a physical location of the animal, said transceiver being electrically coupled to said control circuit such that the physical location of the animal is continuously updated in said database in said electronic memory;
- a hydration monitor being coupled to said collar wherein said hydration monitor is configured to sense the hydration level of the animal, said hydration monitor being positioned on said first side of said outer surface of said collar wherein said hydration monitor is configured to be in physical contact with the animal, said hydration monitor being electrically coupled to said control circuit, said control circuit communicating the hydration level of the animal to said electronic memory;
- a heart monitor being coupled to said first collar wherein said heart monitor is configured to sense the animal's heartbeat, said heart monitor being positioned on said first side of said outer surface of said collar wherein said heart monitor is configured to be in physical contact with the animal, said heart monitor being electrically coupled to said control circuit, said control circuit communication the heartbeat to said electronic memory;
- a display being coupled to said collar, said display being electrically coupled to said control circuit, said display displaying indicia comprising operational parameters of each of said allergen detector, said hydration monitor and said heart monitor, said display being positioned on said second side of said outer surface of said collar wherein said display is configured to be visible to an observer; and
- a power supply being coupled to said collar, said power supply being electrically coupled to said control circuit, said power supply being positioned on said second side of said outer surface of said collar, said power supply comprising at least one battery.

* * * * *